(12) United States Patent
Wei et al.

(10) Patent No.: US 10,507,185 B2
(45) Date of Patent: Dec. 17, 2019

(54) COMPOSITE STRUCTURAL MATERIAL AND PHARMACEUTICAL COMPOSITION THEREOF

(71) Applicant: INNOVACO PHARMACEUTICALS, INC, Beijing (CN)

(72) Inventors: William Shifeng Wei, Ringoes, NJ (US); Herling Uang, Ringoes, NJ (US)

(73) Assignee: INNOVACO PHARMACEUTICALS, INC., Beijing (CN)

( * ) Notice: Subject to any disclaimer, the term of this patent is extended or adjusted under 35 U.S.C. 154(b) by 0 days.

(21) Appl. No.: 14/865,624

(22) Filed: Sep. 25, 2015

(65) Prior Publication Data

US 2016/0074331 A1    Mar. 17, 2016

Related U.S. Application Data

(63) Continuation-in-part of application No. PCT/CN2014/000354, filed on Mar. 31, 2014.

(30) Foreign Application Priority Data

Mar. 29, 2013 (CN) .......................... 2013 1 0106349
Apr. 27, 2013 (CN) .......................... 2013 1 0153547

(51) Int. Cl.
*A61K 9/20* (2006.01)
*A61K 31/366* (2006.01)
*A61K 31/404* (2006.01)

(52) U.S. Cl.
CPC ............ *A61K 9/2054* (2013.01); *A61K 9/205* (2013.01); *A61K 9/2013* (2013.01); *A61K 9/2031* (2013.01); *A61K 9/2068* (2013.01); *A61K 9/2095* (2013.01); *A61K 31/366* (2013.01); *A61K 31/404* (2013.01)

(58) Field of Classification Search
CPC .. A61K 9/2054; A61K 31/404; A61K 31/366; A61K 9/2031; A61K 9/2095; A61K 9/2068; A61K 9/205; A61K 9/2059; A61K 9/2013
See application file for complete search history.

(56) References Cited

U.S. PATENT DOCUMENTS

| | | | | |
|---|---|---|---|---|
| 2005/0042290 A1* | 2/2005 | Kerc | ................. | A61K 9/2027 424/471 |
| 2008/0145427 A1* | 6/2008 | Berchielli | ............ | A61K 9/0004 424/484 |
| 2009/0110728 A1* | 4/2009 | Rastogi | .................. | A61K 9/209 424/468 |
| 2010/0310607 A1* | 12/2010 | Ju | ........................ | A61K 9/1623 424/400 |

FOREIGN PATENT DOCUMENTS

| | | |
|---|---|---|
| CN | 1080169 A | 1/1994 |
| CN | 101919817 A | 12/2010 |
| EP | 2979707 A1 | 2/2016 |
| KR | 20110086944 A | 8/2011 |

OTHER PUBLICATIONS

CN 1080169 translation.*
Zamboni et al. (CN1080169) english translation.*
Zamboni et al. (CN 1080169 A) English translation.*
Zamboni et al. (CN 1080169 A) English translation (Year: 1994).*
CN104069502A office action dated Oct. 1, 2014 to Innovaco Pharmaceuticals, Inc.

* cited by examiner

*Primary Examiner* — Aradhana Sasan
*Assistant Examiner* — Quanglong N Truong
(74) *Attorney, Agent, or Firm* — Flener IP & Business Law; Zareefa B. Flener

(57) ABSTRACT

A composite structural material and pharmaceutical composition comprising same, the use of the composite structural material in preparing a sustained release formulation, and a pharmaceutical composition formulation method; the composite structural material comprises a hydrophobic structural material and a hydrophilic structural material; the proportion of the hydrophobic structural material to the hydrophilic structural material ranges from 1:0.01 to 1:5, preferably 1:0.05 to 1:4, more preferably 1:0.1 to 1:3, and most preferably 1:0.4 to 1:2, such as 1:0.4 to 1:1.3. The pharmaceutical composition comprises the composite structural material and one or more active pharmaceutical ingredients, and preferably the proportion of the composite structural material to the active pharmaceutical ingredients ranges from 1:0.01 to 1:8, more preferably 1:0.02 to 1:5, and most preferably 1:0.03 to 1:1, such as 1:0.3 to 1:0.7.

8 Claims, No Drawings

COMPOSITE STRUCTURAL MATERIAL AND PHARMACEUTICAL COMPOSITION THEREOF

CROSS-REFERENCE TO RELATED APPLICATION

The application is a continuation in part of PCT/CN2014/000354 (filed on Mar. 31, 2014), which claims priority of CN. patent Application Serial No. 201310106349.9 (filed on Mar. 29, 2013) and priority of CN. patent Application Serial No. 201310153547.0 (filed on Apr. 27, 2013), the contents of which are incorporated herein by reference in their entirety.

FIELD OF THE INVENTION

The present invention relates generally to pharmaceutical formulation, and more specifically, relates to a composite structural material and pharmaceutical composition comprising same, and the usage of the composite structural material in preparing sustained release formulation.

BACKGROUND OF THE INVENTION

Sustained release formulation, particularly in tablet and in capsule forms, is a very useful formulation that can reduce the frequency of administration and can control drug level in blood to sustain pharmacological effect. For example, sustained release formulation can change the dose frequency of the drugs such as ibuprofen, phenylpropanolamine hydrochloride, fluvastatin, lovastatin and so on from several times daily in general to once or twice daily.

As a method of preparing a sustained release formulation, it is widely recognized that various hydrophilic polymer materials can be used as sustained release matrix. For example, a fluvastatin sustained-release tablet, described in CN Pat. No. ZL 200780014499.X and CN Pat. No. ZL 99812081.2, is prepared by comprising active pharmaceutical ingredients, water encounter swelling hydrophilic structural materials and other excipients. When this medicine is taken, water insinuates into tablet to dissolve active pharmaceutical ingredients, and make hydrophilic structural materials swell to form high viscosity gel; then the dissolved pharmaceuticals can be delayed-released through the high viscosity gel. At present, sustained release formulation have a high amount of hydrophilic polymer materials in general, water encounter swelling of which easily causes problems in the production and storage of drugs, such as more waste produced, difficulty to form film coating or that the stability of some drugs is affected in storage since sustained release tablets absorb water easily.

As another method, that osmotic pump technology is used to prepare sustained release formulation is disclosed in prior art, such as a lovastatin sustained-release tablet described in U.S. Pat. No. 5,916,595. In this method, active pharmaceutical ingredients, osmotic pressure regulators and other excipients are prepared the tablet core; since lovastatin is practically insoluble in water, all the materials in the tablet core should be hydrophilic, which causes producing more waste, making film coating difficult and easily absorbing water to affect drug stability. In addition, large amounts of organic solvents should be used to dissolve coating materials when the tablet core film-coating. The use of large amounts of organic solvents in drug production is easy to cause environmental pollution and security risks. Laser drilling, the process of which is complicate and the rejection rate of which is high, is needed after film coating.

Generally, the sustained release formulation contains low water-soluble even water-insoluble active pharmaceutical ingredients, which excipient materials especially the sustained-release structural materials are all hydrophilic. In addition, for high water-soluble, low water-soluble even water-insoluble active pharmaceutical ingredients, the preparation of sustained release formulation containing heavy doses of the active pharmaceutical ingredients is very difficult.

For the active pharmaceutical ingredients having lower or higher pKa value, the pH of dissolution medium has great influence on solubility and dissolution of drugs, so the preparation of sustained release formulation having high content of the active pharmaceutical ingredients is also very difficult.

Therefore, it is necessary to develop new sustained release formulations to solve one or more problems in prior art.

SUMMARY OF THE INVENTION

The present invention provides a composite structural material comprising a hydrophobic structural material and a hydrophilic structural material, wherein, the proportion of the hydrophobic structural material to the hydrophilic structural material ranges from 1:0.01 to 1:5, preferably 1:0.05 to 1:4, more preferably 1.0.1 to 1:3, most preferably 1:0.4 to 1:2, such as 1:0.4 to 1:1.3.

The present invention also provides a method of preparing a composite structural material comprising: mixing a hydrophobic structural material and a hydrophilic structural material, and the proportion of the hydrophobic structural material to the hydrophilic structural material ranges from 1:0.01 to 1:5, preferably 1:0.05 to 1:4, more preferably 1:0.1 to 1:3, most preferably 1:0.4 to 1:2, such as 1:0.4 to 1:1.3.

Preferably, the hydrophilic structural material is a composite hydrophilic structural material including a plurality of hydrophilic structural materials of varied viscosity; more preferably, the composite hydrophilic structural material includes a hydrophilic structural material of high viscosity and a hydrophilic structural material of low viscosity; further preferably, the proportion of the hydrophilic structural material of high viscosity to the hydrophilic structural material of low viscosity ranges from 1:0.01 to 1:10, preferably 1:0.05 to 1:8, more preferably 1:0.3 to 1:4, most preferably 1:1 to 1:3.

The present invention also provides a usage of the composite structural material described herein in preparing pharmaceutical sustained release formulation, preferably, the release time of the prepared sustained release formulation in water or in intestinal pH (e.g., pH 4-8) after the administration reaches 4 to 24 h, preferably 6 to 20 h, more preferably 8 to 18; preferably, the release rate at the 0.5th hour of the prepared sustained release formulation (e.g., the prepared fluvastatin sustained-release tablet in this invention) in dissolution medium by reference to the test method as stated in Appendix XD and Appendix XC of Chinese Pharmacopoeia (2010) is within 15%, such as within 10%; the release rate at the 2nd hour is 1-40%, preferably 5-35%; the release rate at the 4th hour is 10-70%, preferably 15-60%; the release rate at the 6th hour is 20-90%, preferably 30-88%; the release rate at the 8th hour is not less than 80%.

The present invention also provides a composite hydrophilic structural material comprising a plurality of hydrophilic structural materials of varied viscosity; preferably, the composite hydrophilic structural material is comprised of a hydrophilic structural material of high viscosity and a hydrophilic structural material of low viscosity; preferably, the proportion of the hydrophilic structural material of high viscosity to the hydrophilic structural material of low viscosity ranges from 1:0.01 to 1:10, preferably 1:0.05 to 1:8, more preferably 1:0.3 to 1:4, most preferably 1:1 to 1:3.

The present invention also provides a usage of a composite hydrophilic structural material in combination with a hydrophobic structural material in preparing a pharmaceutical composition, wherein, the proportion of the hydrophobic structural material to the composite hydrophilic structural material ranges from 1:0.01 to 1:5, preferably 1:0.05 to 1:4, more preferably 1:0.1 to 1:3, most preferably 1:0.4 to 1:2.

The present invention also provides a pharmaceutical composition comprising the composite structural material of this invention and one or more active pharmaceutical ingredients, preferably the proportion of the composite structural material to the active pharmaceutical ingredients ranges from 1:0.01 to 1:8, more preferably 1:0.02 to 1:5, most preferably 1:0.03 to 1:1, such as 1:0.3 to 1:0.7.

The present invention also provides a method of preparing the pharmaceutical composition of this invention comprising:

(1) mixing a hydrophobic structural material and a hydrophilic structural material to obtain a composite structural material, wherein, the proportion of the hydrophobic structural material to the hydrophilic structural material is 1:0.01 to 1:5, preferably 1:0.05 to 1:4, more preferably 1:0.1 to 1:3, most preferably 1:0.4 to 1:2, such as 1:0.4 to 1:1.3;

(2) mixing the composite structural material, one or more active pharmaceutical ingredients and one or more options of conventional pharmaceutically acceptable carriers, adjuvants and media to obtain a pharmaceutical composition, wherein, the proportion of the composite structural material to the active pharmaceutical ingredients is preferably 1:0.01 to 1:8, more preferably 1:0.02 to 1:5, most preferably 1:0.03 to 1:1, such as 1:0.3 to 1:0.7; and (3) optionally, using the pharmaceutical composition to prepare suitable dosage forms, such as granulating and tabletting.

DETAILED DESCRIPTION OF THE INVENTION

The present invention provides a composite structural material comprising a hydrophobic structural material and a hydrophilic structural material, wherein, the proportion of the hydrophobic structural material to the hydrophilic structural material ranges from 1:0.01 to 1:5, preferably 1:0.05 to 1:4, more preferably 1:0.1 to 1:3, most preferably 1:0.4 to 1:2, such as 1:0.4 to 1:1.3.

The hydrophobic structural material comprises two or more hydrophobic structural materials of different melting points, different acid values or different solubilities in ethanol according to the arbitrary proportion.

The hydrophilic structural material comprises two or more hydrophilic structural materials according to the arbitrary proportion.

In one embodiment of the invention, a composite structural material is provided comprising a hydrophobic structural material and a hydrophilic structural material, wherein, the proportion of the hydrophobic structural material to the hydrophilic structural material ranges from 1:0.01 to 1:5, preferably 1:0.05 to 1:4, more preferably 1:0.1 to 1:3, most preferably 1:0.4 to 1:2, such as 1:0.4 to 1:1.3.

Unless otherwise specified, all proportions or percentages used herein account by weight.

"The hydrophobic structural materials", as the term used herein, include non-soluble structural materials and biodegradable structural materials, and the non-soluble structural materials and the biodegradable structural materials are as thereinafter defined. Preferably, the Hydrophilic Lipophilic Balance (HLB) value of the hydrophobic structural materials is less than 11, preferably less than 9, more preferably less than 7. Preferably, the number average molecular mass of the hydrophobic structural materials ranges from approximately 100 Da to approximately 7,000,000 Da, more preferably approximately 200 Da to approximately 5,000,000 Da, further more preferably approximately 250 Da to approximately 3,000,000 Da.

"The non-soluble structural materials", as the term used herein, refer to water-insoluble high polymer materials and so on, of which the instances include ethyl cellulose (EC), polyethylene (PE), polypropylene (PP), polysiloxane, polyvinyl chloride (PVC), ethylene/vinyl acetate copolymer (EVA), polymethyl methacrylate (PMMA) or mixtures thereof.

"The biodegradable structural materials", as the term used herein, include biodegradable structural materials that have low melting point (e.g., melting point of less than 200° C.), insoluble in water but soluble in organic solvents (e.g., chloroform or acetone) or that have low HLB value (e.g., the HLB value of less than 9). The instances of the biodegradable structural materials include waxy, fatty acid and ester thereof and so on, for instance, $C_{16}$-$C_{22}$ fatty acid, carnauba wax, glycerides of $C_{16}$-$C_{22}$ fatty acid, $C_{16}$-$C_{22}$ alkyl alcohols, beewax, synthetic wax, hydrogenated vegetable oil, or mixtures thereof; preferably carnauba wax, glycerides of $C_{16}$-$C_{22}$ fatty acid (include $C_{16}$-$C_{22}$ fatty glyceride, $C_{16}$-$C_{22}$ fatty diglyceride and $C_{16}$-$C_{22}$ fatty monoglyceride). The glyceride of $C_{16}$-$C_{22}$ fatty acid is selected from at least one of the following types: glyceryl behenate, diglyceryl behenate, mono glyceryl behenate, and mixtures thereof.

"The hydrophilic structural materials", as the term used herein, refer to the structural materials that will swell to form gel barrier when encountering water or aqueous solutions such as digestive juices. The instances include natural plant or animal glue, such as sodium alginates, agar, tragacanth, xanthan gum, pectin, guar gum and so on; cellulose derivative, such as methyl cellulose (MC), hydroxyethyl cellulose (HEC), hydroxyethyl methyl cellulose (NEMC), hydroxy propyl cellulose (HPC), hydroxypropyl methylcellulose (HPMC), sodium carboxymethylcellulose (SCMC) and so on; noncellulosic polysaccharide, such as chitin, galactomannan, glucan and so on; ethylene polymers and acrylic resin, such as polyethylene oxide (PEO), crospolyvinylpyrrolidone, polyvinyl alcohol (PVA) and carboxy polymethylene (CP) and so on. Preferably, the hydrophilic structural materials include but are not limited to the dissociated or non dissociated high polymer materials that will swell when encountering water such as hydroxypropyl methylcellulose (HPMC), hydroxy propyl cellulose (HPC), hydroxyethyl cellulose (HEC), sodium carboxymethylcellulose (SCMC), sodium alginates, chitin, polyethylene oxide (PEO). More preferably, the hydrophilic structural materials are hydroxypropyl methylcellulose (HPMC), hydroxy propyl cellulose (HPC), hydroxyethyl cellulose (HEC), sodium carboxymethylcellulose (SCMC). Preferably, the number average molecular mass of the hydrophilic structural materials used herein range from approximately 50 Da to approximately 9,000.00 Da, preferably approximately 50,000 Da to approximately 8,000,000 Da, more preferably approximately 90,000 Da to 7,000,000 Da. Specifically the number average molecular mass of cellulose derivatives of the hydrophilic structural materials used herein range from approximately 50 Da to approximately 2,500,000 Da, more preferably approximately 70 Da to approximately 2,000,000 Da, most preferably approximately 80 Da to approximately 1,800,000 Da. The number average molecular mass of polyethylene oxide (PEO) of the hydrophilic structural materials used herein ranges from approximately 50,000 Da to approximately 8,000,000 Da, more preferably approximately 100,000 Da to approximately 7,000,000 Da.

Preferably the instances of the hydrophilic structural materials of high viscosity are the hydrophilic structural materials of the viscosity ranges from 4,000 mPa·s to 100,000 mPa·s, such as hydroxypropyl methylcellulose (HPMC) 75HD15000 (or K15M).

Preferably the instances of the hydrophilic structural materials of low viscosity are the hydrophilic structural materials of the viscosity less than 1,000 mPa·s, such as hydroxypropyl methylcellulose (HPMC) 75HD100 (or K100LV).

"Viscosity", as the term used herein, refers to the viscosity of the solution obtained by 2 g substance dissolving in 100 mL of distilled water at 20° C., of which the unite is mPa·s. "Low viscosity" used herein refers to that the viscosity of the hydrophilic structural material is 20-2,000 mPa·s, preferably 20-800 mPa·s, more preferably 20-600 mPa·s. "High viscosity" used herein refers to that the viscosity of the hydrophilic structural material is 3,000-500,000 mPa·s, preferably 3,500-300,000 mPa·s, more preferably 4,000-200,000 mPa·s.

The present invention provides a method of preparing a composite structural material comprising: mixing a hydrophobic structural material and a hydrophilic structural material according to the proportion ranging from 1:0.01 to 1:5, preferably 1:0.05 to 1:4, more preferably 1:0.1 to 1:3, most preferably 1:0.4 to 1:2, such as 1:0.4 to 1:1.3;

preferably, the hydrophilic structural material is a composite hydrophilic structural material including a plurality of hydrophilic structural materials of varied viscosity; more preferably, the hydrophilic structural material includes a hydrophilic structural material of high viscosity and a hydrophilic structural material of low viscosity; further preferably, the proportion of the hydrophilic structural material of high viscosity to the hydrophilic structural material of low viscosity ranges from 1:0.01 to 1:10, preferably 1:0.05 to 1:8, more preferably 1:0.3 to 1:4, most preferably 1:1 to 1:3.

The present invention also provides a usage of the composite structural material described herein in preparing pharmaceutical sustained release formulation, preferably, the release time of the prepared sustained release formulation in water or in intestinal pH (e.g., pH 4-8) after the administration reaches 4 to 24 h, preferably 6 to 20 h, more preferably 8 to 18; preferably, the release rate at the 0.5th hour of the prepared sustained release formulation (e.g., the prepared fluvastatin sustained-release tablet in this disclosure) in dissolution medium by reference to the test method as stated in Appendix XD and Appendix XC of Chinese Pharmacopoeia (2010) is within 15%, such as within 10%; the release rate at the 2nd hour is 1-40%, preferably 5-35%; the release rate at the 4th hour is 10-70%, preferably 15-60%; the release rate at the 6th hour is 20-90%, preferably 30-88%; the release rate at the 8th hour is not less than 80%.

The composite structural material of this invention is available for sustained release formulations to avoid that active pharmaceutical ingredients release a lot untimely.

The present invention also provides a composite hydrophilic structural material comprising a plurality of hydrophilic structural materials of varied viscosity; preferably, the composite hydrophilic structural material is comprised of a hydrophilic structural material of high viscosity and a hydrophilic structural material of low viscosity; preferably, the proportion of the hydrophilic structural material of high viscosity to the hydrophilic structural material of low viscosity used herein ranges from 1:0.01 to 1:10, preferably 1:0.05 to 1:8, more preferably 1:0.3 to 1:4, most preferably 1:1 to 1:3.

The present invention also provides a usage of a composite hydrophilic structural material in combination with a hydrophobic structural material in preparing a pharmaceutical composition, and the proportion of the hydrophobic structural material to the composite hydrophilic structural material ranges from 1:0.01 to 1:5, preferably 1:0.05 to 1:4, more preferably 1:0.1 to 1:3, most preferably 1:0.4 to 1:2, such as 1:0.4 to 1:1.3.

The present invention also provides a pharmaceutical composition comprising the composite structural material of this invention and one or more active pharmaceutical ingredients, preferably the proportion of the composite structural material to the active pharmaceutical ingredients ranges from 1:0.01 to 1:8, more preferably 1:0.02 to 1:5, most preferably 1:0.03 to 1:1, such as 1:0.3 to 1:0.7.

The active pharmaceutical ingredient can include one or more substances, of which the total content (in a unit dosage) is 0.02 mg to 1 g, and that has the following properties:

the solubility of which in water (at 37° C.) is in the range of 0 to more than 50 mg/mL; and/or the solubility of which in pH 6.8 buffer (at 37° C.) is in the range of 0 to more than 50 mg/mL; and/or the solubility of which in pH 1.2 buffer (at 37° C.) is in the range of 0 to more than 50 mg/mL; and/or which belongs to the range of un-ionized drug to ionized form or pharmaceutically acceptable salts thereof; For ionized drug, the pKa value is the range of 2 to 14, preferably 4 to 12; and/or the oil-water partition coefficient is the range of 0.05 to 10, preferably 1 to 8.

Stated are the active pharmaceutical ingredients such as fluvastatin, atorvastatin, lovastatin, mesalazine, paroxetine, tolterodine, dalfampridine, gabapentin, venlafaxine (VEN), divalproex sodium, tamsulosin, alfuzosin, carbamazepine, quetiapine, chlorpheniramine, isradipine, doxazosin, methylphenidate, paliperidone, prazosin or pramipexole, or pharmaceutically acceptable salts thereof; preferably fluvastatin, atorvastatin, lovastatin, mesalazine, paroxetine, tolterodine or pramipexole, or pharmaceutically acceptable salts thereof.

In one embodiment, the content of the hydrophobic structural material based on the total weight of the pharmaceutical composition is 1%-30%, preferably 3%-25%, more preferably 5%-22%, most preferably 16-20%.

In one embodiment, the content of the hydrophilic structural material based on the total weight of the pharmaceutical composition is 1%-30%, preferably 1%-25%, more preferably 2%-24%, most preferably 8-23%.

In one embodiment of pharmaceutical composition in this invention, the proportion of the hydrophobic structural material to the hydrophilic structural material ranges from 1:0.01 to 1:5, preferably 1:0.05 to 1:4, more preferably 1:0.1 to 1:3, most preferably 1:0.4 to 1:2, such as 1:0.4 to 1:1.3.

In one embodiment, the hydrophilic structural material can include the hydrophilic structural material of low viscosity (e.g., hydroxypropyl methylcellulose (HPMC) with the viscosity of 100 mPa·s) and that of high viscosity (e.g., hydroxypropyl methylcellulose (HPMC) with the viscosity of 15000 mPa·s).

In one embodiment, the proportion of the hydrophilic structural material of high viscosity to the hydrophilic structural material of low viscosity used herein ranges from 1:0.01 to 1:10, preferably 1:0.05 to 1:8, more preferably 1:0.1 to 1:6, most preferably 1:0.3 to 1:4, such as 1:1 to 1:3.

In one embodiment, the pharmaceutical composition can contain water-soluble excipients, such as lactose, sodium chloride, polyethylene glycol and so on, of which the content based on the total weight of the pharmaceutical composition is 2%-30%, preferably 5%-25%.

In one embodiment, the pharmaceutical composition can contain water-insoluble excipients, such as calcium phosphate, of which the content based on the total weight of the pharmaceutical composition is 1%-50%, preferably 10%-40%.

The pharmaceutical composition can or can't contain one or more conventional pharmaceutically acceptable carriers, adjuvants and media, for instance, surfactants such as sodium lauryl sulphate, tween and so on; diluents, excipients or fillers such as starch, calcium carbonate, calcium phosphate, lactose, microcrystalline cellulose and so on; osmotic pressure regulators such as sucrose, sodium chloride and so on; pH regulators such as citric acid, sodium bicarbonate and so on; lubricants such as calcium stearate or magnesium stearate and so on; slip agents such as talcum powder; film coating materials such as polyacrylic acid resin; and other adjuvants such as fragrances and sweeteners and/or colorants.

The present invention also provides a method of preparing the pharmaceutical composition of this invention comprising:

(1) mixing a hydrophobic structural material and a hydrophilic structural material to obtain a composite structural material, wherein, the proportion of the hydrophobic structural material to the hydrophilic structural material is 1:0.01 to 1:5, preferably 1:0.05 to 1:4, more preferably 1:0.1 to 1:3, most preferably 1:0.4 to 1:2, such as 1:0.4 to 1:1.3; preferably, the hydrophilic structural materials is a composite hydrophilic structural material including a plurality of hydrophilic structural materials of varied viscosity; more preferably, the hydrophilic structural material is comprised of a hydrophilic structural material of high viscosity and a hydrophilic structural material of low viscosity; further preferably, the proportion of the hydrophilic structural material of high viscosity to the hydrophilic structural material of low viscosity used herein ranges from 1:0.01 to 1:10, preferably 1:0.05 to 1:8, more preferably 1:0.3 to 1:4, most preferably 1:1 to 1:3;

(2) mixing the composite structural material, one or more active pharmaceutical ingredients and one or more options of conventional pharmaceutically acceptable carriers, adjuvants and media to obtain a pharmaceutical composition, wherein, the proportion of the composite structural material to the active pharmaceutical ingredients is preferably 1:0.01 to 1:8, more preferably 1:0.02 to 1:5, most preferably 1:0.03 to 1:1, such as 1:0.3 to 1:0.7; and (3) optionally, using the pharmaceutical composition to prepare suitable dosage forms, such as granulating and tabletting.

The pharmaceutical composition preparation method is pressing the active pharmaceutical ingredients and the excipients into a tablet via conventional dry granulation, wet granulation, melt granulation, or direct compression and so on. The completed tablets are film coated. The drugs that are stomach-stimulating or that are unstable in gastric juice are also enteric coated. The drugs with light, heat or water instability are also protective coated.

Therefore, the pharmaceutical composition can be made into known formulations for administration, and the formulations include but not limited to capsules, tablets, powders and granules. The formulations are prepared according to the familiar technologies in the pharmaceutical preparation field. For example, tablets are prepared via direct compression, and/or multilayer tablet and/or tablet-in-tablet technologies.

In one embodiment, the release time of the sustained release formulation prepared by the pharmaceutical composition of this invention in vitro can reach 4 h to 24 h, preferably 6 h to 20 h, more preferably 8 h to 18 h.

In one embodiment, the release rate at the 0.5th hour of the prepared sustained release formulation (e.g., the prepared fluvastatin sustained-release tablet described herein) in dissolution medium according to the test method as stated in Appendix XD and Appendix XC of Chinese Pharmacopoeia (2010) is within 15%, such as within 10%; the release rate at the 2nd hour is 1-40%, preferably 5-35%; the release rate at the 4th hour is 10-70%, preferably 15-60%; the release rate at the 6th hour is 20-90%, preferably 30-88%; the release rate at the 8th hour is not less than 80%.

Compared with the prior art, the invention may have the advantages as following:

(1) reducing the content of the hydrophilic structural materials swelling when encountering water, therefore reducing the water effects on the quality of pharmaceutical preparations, and/or (2) simplifying the production process, lowering the production cost and non-using organic solvents when the composite structural material is used to prepare sustained release formulation; and/or (3) that the composite structural material can be applied to prepare sustained release formulation containing heavy doses of active pharmaceutical ingredients, high water-soluble and low water-soluble even insoluble active pharmaceutical ingredients; and/or (4) that the composite structural material can be applied to prepare sustained release formulation containing heavy doses of the un-ionized or ionized forms in water of active pharmaceutical ingredients.

Each embodiment or that of different preferable level described herein can be combined at will unless otherwise specified.

The following embodiments are representative of several aspects of the disclosure disclosed herein, and are not intended to limit the scope of what the inventors regard as their disclosure. All the implementation techniques based on the above in this disclosure belong to the scope of the invention. The compounds and reagents used in the following embodiments can be purchased commercially, or can be prepared via conventional methods known by the skilled person; the laboratory apparatus used can be purchased commercially.

Embodiments

Embodiment 1: Preparation of Lovastatin Sustained-release Tablets

TABLE 1

Components of Lovastatin Sustained-release Tablets

| Serial Number, S/N | Components | Weight (g) |
|---|---|---|
| 1 | lovastatin | 5 |
| 2 | glyceryl behenate | 10 |
| 3 | hydroxypropyl methylcellulose/HPMC (75HD15000) | 1 |
| 4 | hydroxypropyl methylcellulose/HPMC (75HD100) | 3 |
| 5 | calcium phosphate | 19 |
| 6 | lactose | 10 |
| 7 | corn starch | 1 |
| 8 | magnesium stearate | 0.5 |
| 9 | talcum powder | 0.5 |
| | In total | 50 |

Lovastatin was purchased from Yantai Zhichu Pharmaceuticals Co., Ltd; glyceryl behenate was purchased from Aceda (Chengdu) Chemical Reagent Co., Ltd or Gattefosse (France) Co.; various hydroxypropyl methylcelluloses (HPMC) were all purchased from Shandong Heda Corp., Ltd; calcium phosphate was purchased from Huzhou Zhanwang Pharmaceuticals Co., Ltd.

According to the components of Table 1, lovastatin and excipients in the range from #2 to #6 were weighed separately and then mixed together for 1 minute in high shearing mixing granulator. To the mixture corn starch paste made of #7 was added and granulated. The granulated particles were size stabilized following drying. The size-stabilized granules were put in the mixer. To the granules magnesium stearate and talcum powder were added and mixed together for 1 minute. The obtained mixture was made into tablets weighing 200 mg by tablet press. The tablets could also be coated by polyacrylate resin.

Contrasting Embodiment 1: Preparation of Lovastatin Sustained-release Tablets

According to the components of Table 1, the same dosages of calcium phosphate instead of glyceryl behenate were added to prepare lovastatin sustained-release tablets in the way of Embodiment 1.

Contrasting Embodiment 1: Preparation of Lovastatin Sustained-release Tablets

According to the components of Table 1, the same dosages of calcium phosphate instead of hydroxy propyl cellulose (HPC) #3 and #4 were added to prepare lovastatin sustained-release tablets in the way of Embodiment 1.

Release Rate Determination of Lovastatin Sustained-Release Tablets

The dissolution medium, which is pH 7.0 phosphate solution containing 2% sodium lauryl sulfate, was prepared by reference to the test method as stated in Appendix XD and Appendix XC of Chinese Pharmacopoeia (2010).

To a 900 mL dissolution medium at 37° C. the lovastatin sustained-release tablets were added and mixed by using the oar method in 50 rpm. The proper amount of the solution was sampled in the time frame given and filtered to determinate the contents. The corresponding release rate of embodiment 1 product, Contrasting embodiment 1 product, contrasting embodiment 2 product and the commercial product (ALTOPREV®, American ANDRX Co.) were determinated respectively. The result of release rate of the lovastatin sustained-release tablets was summarized in Table 2 (Each data was the average of six measured data). Seen from Table 2, the sustained-release tablets of this invention exhibited more stable and equal release rate compared to other sustained-release tablets used in this trial. It was also indicated from Table 2 that the sustained-release tablets prepared by using the composite structural material of this invention was superior to that prepared by using any single sustained-release material. It was further indicated from Table 2 that the sustained-release tablets of this invention had the comparable release rate with the commercial product ALTOPREV® while the both applied different structural materials and technologies.

TABLE 2 the Release Rate of Lovastatin Sustained-release Tablets

| Time (h) | Embodiment 1 (%) | Contrasting Embodiment 1 (%) | Contrasting Embodiment 2 (%) | ALTOPREV ® (%) |
|---|---|---|---|---|
| 0.5 | 0.7 | 10 | 22 | 0.2 |
| 2 | 8 | 20 | 30 | 5 |
| 3 | 15 | 45 | 50 | 12 |
| 4 | 19 | 60 | 65 | 22 |
| 6 | 34 | 90 | 90 | 45 |
| 8 | 48 | 98 | — | 62 |
| 12 | 63 | — | — | 80 |
| 16 | 78 | — | — | 82 |
| 20 | 90 | — | — | 83 |

Embodiment 2: Preparation of Fluvastatin Sustained-release Tablets

TABLE 3

Components of Fluvastatin Sustained-release Tablets

| Serial Number, S/N | Material Name | Weight (g) |
|---|---|---|
| 1 | fluvastatin | 13.3 |
| 2 | glyceryl behenate | 8 |
| 3 | hydroxypropyl methylcellulose/HPMC (75HD100) | 5 |
| 4 | hydroxypropyl methylcellulose/HPMC (75HD15000) | 5 |
| 5 | calcium phosphate | 5 |
| 6 | lactose | 11.7 |
| 7 | corn starch | 1 |
| 8 | magnesium stearate | 0.5 |
| 9 | talcum powder | 0.5 |
| | In total | 50 |

In an embodiment, fluvastatin was purchased from Indian Aurobindo Pharma Ltd; glyceryl behenate was purchased from Aceda (Chengdu) Chemical Reagent Co., Ltd or Gattefosse (France) Co.; various hydroxypropyl methylcelluloses (HPMC) were all purchased from Shandong Heda Corp., Ltd; calcium phosphate was purchased from Huzhou Zhanwang Pharmaceuticals Co., Ltd.

According to the components of Table 3, fluvastatin and excipients in the range from #2 to #6 were weighed separately and then mixed together for 1 minute in high shearing mixing granulator. To the mixture corn starch paste made of #7 was added and granulated. The granulated particles were size stabilized following drying. The size-stabilized granules were put in the mixer. To the granules magnesium stearate and talcum powder were added and mixed together for 1 minute. The obtained mixture was made into tablets weighing 305 mg by tablet press. The tablets could also be coated by polyacrylate resin.

Release Rate Determination of Fluvastatin Sustained-release Tablets

Determination by reference to the test method as stated in Appendix XD and Appendix XC of Chinese Pharmacopoeia (2010).

To a 1000 mL water at 37° C. the fluvastatin sustained-release tablets were added and mixed by using the basket method in 50 rpm. The proper amount of the solution was sampled in the time frame given and filtered to determinate the contents. The corresponding release rate of Embodiment 2 product and the commercial product of fluvastatin sustained-release tablets (Lescol®, Beijing Novartis Pharma Ltd) were determinated respectively. The result of release rate of the fluvastatin sustained-release tablets was summarized in Table 4 (Each data was the average of six measured data). From Table 4, the sustained-release tablets of this invention had the similar release rate with the commercial product while the both applied different structural materials.

TABLE 4 the Release Rate of Fluvastatin Sustained-release Tablets

| Time (h) | Embodiment 2 (%) | Lescol ® (%) |
|---|---|---|
| 0.5 | 8.7 | 6.0 |
| 2 | 30.3 | 26.0 |
| 4 | 59.0 | 54.8 |
| 6 | 86.9 | 86.2 |
| 8 | 109.2 | 112.6 |

Embodiment 3: Swelling Degree of the Structural Materials

To a 100 mL beaker 1 g of per structural material shown in the table 5 below were added and mixed with 80 mL purified water. The solution was applied to determinate the swelling degree of the structural materials (Divide swelling height variation by original height). The results are shown in Table 5.

TABLE 5 the Swelling Rate of the Structural Material

| | Structural Material | | | | | |
|---|---|---|---|---|---|---|
| | Glyceryl behenate | Carnauba wax | Hydroxyethyl cellulose | Hydroxypropyl methylcellulose | Xanthan gum | Polyethylene oxide (PEO) |
| Swelling degree (%) | 0 | 0 | 600 | 400 | 280 | 250 |

The results showed that the swelling degree of glyceryl behenate and carnauba wax was the lowest and that of xanthan gum and polyethylene oxide (PEO) was taken second place. The sustained-release structural material adding a low-swelling material was not bibulous to cause the product swelling and deformating. It was also indicated that the releasing mechanism of the sustained-release structural material adding the low-swelling material differed from that of the sustained-release structural material easy to absorb water and to swell.

Embodiment 4: Relations between the Structural Material and the Pelleting Reject Rate The structural materials shown in the table below and calcium phosphate were weighed separately in the proportion of 1:2 and then mixed together for 1 minute in high shearing mixing granulator. To the mixture corn starch paste was added and granulated. The granulated particles were size stabilized following drying. The big granules sifted out by 1 mm sieve were considered to be wastes. The reject rate of each structural material after pelleting was listed in Table 6. The reject rate of the granules comprising hydrophobic structural materials (e.g., insoluble and waxy sustained-release structural materials) was lower so as to achieve higher yield.

TABLE 6 the Reject Rate of the Structural Material after Pelleting

| | Structural Material comprised in the Granules | | | | | |
|---|---|---|---|---|---|---|
| | Glyceryl behenate | Carnauba wax | Hydroxyethyl cellulose (HEC) | Hydroxypropyl methylcellulose (HPMC) | Xanthan gum | Polyethylene oxide (PEO) |
| Reject Rate (%) | 0.1 | 0.3 | 6 | 5 | 7 | 5 |

Embodiment 5: Dissolution Rate of Different Fluvastatin Sustained-Release Tablets in the Mediun of pH 4.5

The pH of dissolution media has effects on the solubility of ionized drug. Sustained release technique has notable effects on the release rate of ionized drug in the media of various pH. Fluvastatin belongs to ionized drug, of which the pKa value is 4.6.

Fluvastatin sustained-release tablets were prepared by using conventional sustained release technique (hydroxypropyl methylcellulose/HPMC was the structural material), of which the components were shown in Table 7. The tablets weighing 305 mg based on corn starch paste made of #7 as adhesive was prepared by the similar procedure of embodiment 2. The corresponding release rate of conventional fluvastatin sustained-release tablets, fluvastatin sustained-release tablets (Embodiment 2) and the commercial products of fluvastatin sustained-release tablets (Lescol®) in acetate buffer solution of pH 4.5 were determinated by using the release rate determination of embodiment 2 respectively. The release results of the three fluvastatin sustained-release tablets were summarize in Table 8. It was indicated that the release rate of fluvastatin sustained-release tablets prepared by using conventional slow release technique in the media of lower pH was beyond the reach of that of the commercial products of fluvastatin sustained-release tablets and not up to the standard during 0.5 h (which is, less than 10%), and that the release rate of fluvastatin sustained-release tablets of this disclosure in the media of lower pH was comparable to that of the commercial products of fluvastatin sustained-release tablets.

TABLE 7 the Components of Fluvastatin Sustained-release Tablets

| Serial Number, S/N | Material Name | Weight (g) |
|---|---|---|
| 1 | fluvastatin | 13.3 |
| 4 | hydroxypropyl methylcellulose/HPMC (75HD15000) | 5 |
| 5 | calcium phosphate | 16 |
| 6 | lactose | 13.7 |
| 7 | corn starch | 1 |

TABLE 7-continued the Components of Fluvastatin Sustained-release Tablets

| Serial Number, S/N | Material Name | Weight (g) |
|---|---|---|
| 8 | magnesium stearate | 0.5 |
| 9 | talcum powder | 0.5 |
| | In total | 50 |

Fluvastatin was purchased from Indian Aurobindo Pharma Ltd; various hydroxypropyl methylcelluloses (HPMC) were all purchased from Shandong Heda Corp., Ltd; calcium phosphate was purchase from Huzhou Zhanwang Pharmaceuticals Co., Ltd.

TABLE 8 the Release Rate of Different Fluvastatin Sustained-release Tablets (in Acetate Buffer Solution of pH 4.5)

| Time (h) | Embodiment 2 (%) | Conventional sustained-release tablets (%) | Lescol ® (%) |
|---|---|---|---|
| 0.5 | 1.5 | 20 | 0.8 |
| 2 | 3.9 | 28 | 2.6 |
| 4 | 6.3 | 36 | 5.0 |
| 6 | 8.4 | 40 | 7.0 |
| 8 | 9.9 | 57 | 8.9 |

Seen from Table 8, the sustained-release tablets of this invention exhibited more stable and equal release rate in pH 4.5 and didn't cause a sudden and vast release, and the sustained-release tablets of this disclosure had the comparable release rate with the commercial product Lescol® at the same time.

Obviously from the foregoing it will be appreciated that in terms of common technology knowledge and conventional means in this field, various modifications, substitutions or alterations may be made on the premise of breaking away from the above basic technical ideas. Every feature of the technical solution described in this disclosure, what the skilled person can understand, will be put together properly as required.

What is claimed is:

1. A pharmaceutical composition comprising a composite structural material and one or more active pharmaceutical ingredients, wherein the composite structural material comprises a hydrophobic structural material and a hydrophilic structural material, wherein, the proportion of the hydrophobic structural material to the hydrophilic structural material ranges from 1:0.01 to 1:5; the hydrophilic structural material is a composite hydrophilic structural material comprised of a hydrophilic structural material of high viscosity and a hydrophilic structural material of low viscosity;
the proportion of the hydrophilic structural material of high viscosity to the hydrophilic structural material of low viscosity ranges from 1:1 to 1:3;
the active pharmaceutical ingredient is selected from the group consisting of fluvastatin, lovastatin, atorvastatin, and pharmaceutically acceptable salt thereof;
the hydrophobic structural material is selected from the group consisting of carnauba wax, glycerides of $C_{16}$-$C_{22}$ fatty acid from at least one of $C_{16}$-$C_{22}$ fatty glyceride, $C_{16}$-$C_{22}$ fatty diglyceride and $C_{16}$-$C_{22}$ fatty monoglyceride, the glyceride of $C_{16}$-$C_{22}$ fatty acid is selected from at least one of the following types: glyceryl behenate, diglyceryl behenate, mono glyceryl behenate, and mixtures thereof;
the content of the hydrophobic structural material based on the total weight of the pharmaceutical composition is 16-20%;
the proportion of the composite structural material to the active pharmaceutical ingredient ranges from 1:0.3 to 1:0.7;
and, the pharmaceutical composition is a tablet.

2. The pharmaceutical composition of claim 1, wherein, the proportion of the hydrophobic structural material to the hydrophilic structural material ranges from 1:0.4 to 1:1.3.

3. The pharmaceutical composition of claim 1, wherein, the hydrophilic structural material is selected from the group consisting of hydroxypropyl methylcellulose (HPMC), hydroxy propyl cellulose (HPC), hydroxyethyl cellulose (HEC), hydroxyethyl methyl cellulose (HEMC), sodium carboxymethylcellulose (SCMC), sodium alginates, chitin, galactomannan, glucan, polyethylene oxide (PEO), crospolyvinylpyrrolidone, polyvinyl alcohol (PVA) and carboxy polymethylene (CP), agar, tragacanth, xanthan gum, pectin, guar gum, and mixtures thereof.

4. The pharmaceutical composition of claim 1, wherein, the hydrophilic structural material of high viscosity is the hydrophilic structural material of the viscosity ranges from 4,000 mPa·s to 100,000 mPa·s;
the hydrophilic structural material of low viscosity is the hydrophilic structural material of the viscosity less than 1,000 mPa·s.

5. The pharmaceutical composition of claim 1, wherein, the composite structural material is used for preparing pharmaceutical sustained release formulation.

6. The pharmaceutical composition of claim 1 comprising a pharmaceutically acceptable carrier, an adjuvant or a media.

7. The pharmaceutical composition of claim 1, wherein, the content of the hydrophobic structural material based on the total weight of the pharmaceutical composition is 1%-30%; and/or
the content of the hydrophilic structural material based on the total weight of the pharmaceutical composition is 0.1%-30%.

8. The pharmaceutical composition of claim 1, wherein, the preparation method of the pharmaceutical composition including:
(1) mixing a hydrophobic structural material and a hydrophilic structural material to obtain a composite structural material, and the proportion of the hydrophobic structural material to the hydrophilic structural material is 1:0.3 to 1:0.7;
(2) mixing the composite structural material, an active pharmaceutical ingredient and a pharmaceutically acceptable carrier, an adjuvant or a media optionally to obtain a pharmaceutical composition, wherein the proportion of the composite structural material to the active pharmaceutical ingredient is preferably 1:0.01 to 1:8;
(3) optionally using the above pharmaceutical composition to prepare proper dosage form.

* * * * *